United States Patent [19]

Reibel

[11] 4,148,309
[45] Apr. 10, 1979

[54] PERSONAL HYGIENE DEVICE

[76] Inventor: Peter R. Reibel, 4363 Monitor Dr., Indianapolis, Ind. 46220

[21] Appl. No.: 803,210

[22] Filed: Jun. 3, 1977

[51] Int. Cl.² ........................... A61H 1/00; A61H 9/00
[52] U.S. Cl. ............................... 128/24 A; 128/62 A; 128/66
[58] Field of Search ............... 128/24 A, 66, 62 A, 128/172.1

[56] References Cited

U.S. PATENT DOCUMENTS

| | | | |
|---|---|---|---|
| 3,044,465 | 7/1962 | Anderson et al. | 128/62 A |
| 3,401,690 | 9/1968 | Martin | 128/172.1 |
| 3,809,977 | 5/1974 | Balamuth et al. | 128/24 A |
| 3,847,662 | 11/1974 | Massa | 128/24 A |
| 3,870,039 | 3/1975 | Moret et al. | 128/66 |

Primary Examiner—Lawrence W. Trapp
Attorney, Agent, or Firm—Woodard, Weikart, Emhardt & Naughton

[57] ABSTRACT

An oral and personal hygiene device for cleansing portions of the human anatomy by means of ultrasonic vibrations. The disclosed embodiment includes a fluid compartment, an ultrasonic transducer, an ultrasonic implement surrounding the transducer, and a fluid delivery pump which is connected between the compartment and the ultrasonic implement. The fluid delivery pump is operable to fill a human anatomical cavity with fluid and is designed to shut itself off once the cavity has been filled. The ultrasonic implement delivers ultrasonic vibrations from the transducer to the fluid within the cavity whereby ultrasonic vibrations are transmitted in the form of cavitating action to all regions of the cavity for removal of foreign material such as food particles. During this cavitating action, the ultrasonic implement remains virtually stationary and is not required to be moved in and around the cavity to assure cleansing of all areas.

19 Claims, 9 Drawing Figures

PERSONAL HYGIENE DEVICE

BACKGROUND OF THE INVENTION

1. Field of the Invention

This invention relates in general to ultrasonic devices and in particular to ultrasonic oral and personal hygiene devices.

2. Description of the Prior Art

There are many types of devices in which ultrasonic energy has been used to accomplish various objectives. Ultrasonics are used in industry for cleaning components, for welding of plastics and for assembly of parts. Ultrasonics have also found application in the field of body scanning and imaging where ultrasound is the medium. Ultrasonic vibrations have also been used for dental purposes, such as cleaning teeth and stimulating gums.

The devices of U.S. Pat. No. 3,828,770 to Kuris et al.; U.S. Pat. No. 3,840,932 to Balamuth et al.; U.S. Pat. No. 3,676,218 to Sawyer and U.S. Pat. No. 3,563,233 to Bodine disclose ultrasonic devices which incorporate a control portion, a transducer portion, and a member attached to said transducer for cleaning the teeth and stimulating the gums. The ultrasonic vibrations generated by these devices are transmitted into a brush or similar member which moves back and forth in response to the vibrations. In order for such devices to be effective cleansing means, the device must be moved in and around the mouth so that the vibrating bristles will contact all exposed surfaces of the teeth. Inasmuch as no external fluid is injected into the mouth, the entire ultrasonic vibration transmission must be conducted in a more localized area, that being the area between the vibrating bristles and the area being contacted for cleaning. Such devices also do not contain a fluid reservoir which can be filled with different chemical compositions and then pumped into the mouth or other cavity for various medical and cleansing reasons. Because of the fact that these devices must be moved to different locations in order to effectively clean, they are not suitable for use by individuals with certain handicaps and disabilities. For example, individuals who are partially or totally handicapped with respect to their hands and arms may not be able to brush their own teeth as would also be true of small children and retarded persons. In order to brush the teeth of such persons requires another individual such as a nurse aid or family member to attempt to use the cleansing device for the invalid, child or retarded person. The use of these devices by some other individual is awkward as well as uncertain as to its cleansing thoroughness.

A slightly different device, although incorporating the same basic ultrasonic principles, is disclosed by U.S. Pat. No. 3,636,947 issued to Balamuth. This device incorporates a gum stimulator and tooth cleansing member attached to the end of a transducer element which also includes means to produce a stream of either continuous or pulsating fluid which is delivered from a liquid reservoir to the area where the stimulator is positioned. By means of replaceable stimulating members of different design, such a device can have a variety of dental related usages; however, there is still the necessity for some degree of manual dexterity and awareness of where to use the device and how to use the device in order for it to be effective. As previously noted with certain invalids, small children and retarded persons, the ability for manual dexterity as well as the awareness is often not present. The previously noted disadvantages of having someone else use the device on the invalid, small child or retarded person are also present with this design, that being the inability to thoroughly clean the teeth. The device of U.S. Pat. No. 3,645,255 to Robinson also discloses an ultrasonic cleansing and dental device which has a variety of replaceable tips which are designed for different applications. This device also has provisions to introduce a stream of some type of fluid as part of the cleansing action although no reservoir for this fluid is shown by the figures of this patent. The device of Robinson continues to have the same disadvantages as previously mentioned with respect to U.S. Pat. No. 3,636,947.

SUMMARY OF THE INVENTION

An oral and personal hygiene device for cleansing various anatomical cavities which comprises a fluid compartment, means for generating ultrasonic vibrations, an ultrasonic implement and a fluid delivery device connected between the compartment and the ultrasonic implement. The fluid compartment has a drain aperture positioned therein which connects to the fluid delivery device and the means for generating ultrasonic vibrations includes an ultrasonic transducer. The ultrasonic implement which encloses the transducer has a passageway therethrough for the passage of fluid which is delivered from the compartment into the cavity. The ultrasonic implement is constructed of a size and shape so as to be insertable within one of the various anatomical cavities. The fluid delivery device is operable to fill the cavity with fluid from the compartment. The ultrasonic implement communicates ultrasonic vibrations from the transducer to the fluid within the cavity whereby ultrasonic vibrations are transmitted in the form of cavitating action to internal surfaces of the cavity while the ultrasonic implement remains virtually stationary.

One object of the present invention is to provide an improved ultrasonic device for cleansing portions of the human anatomy.

Related objects and advantages of the present invention will be apparent from the following description.

DESCRIPTION OF THE PREFERRED EMBODIMENT

Figure 1:
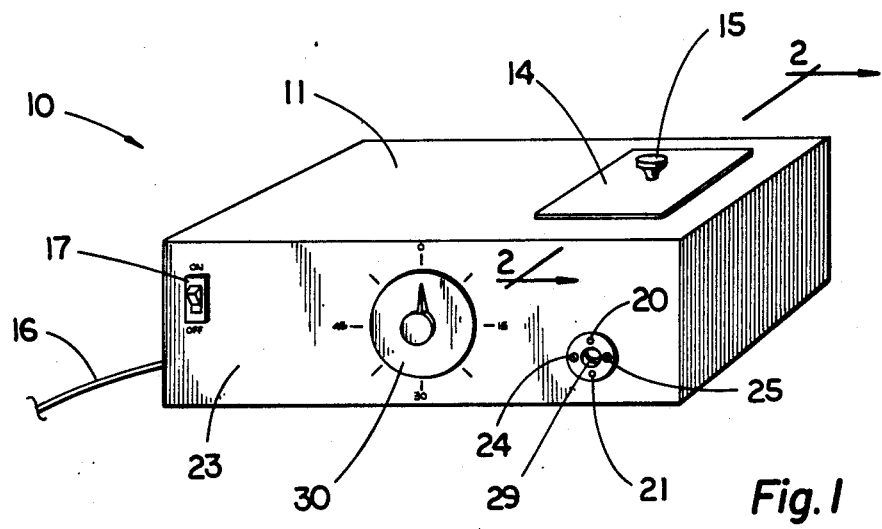
FIG. 1 is a perspective view of a control unit comprising a portion of the personal hygiene device according to the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
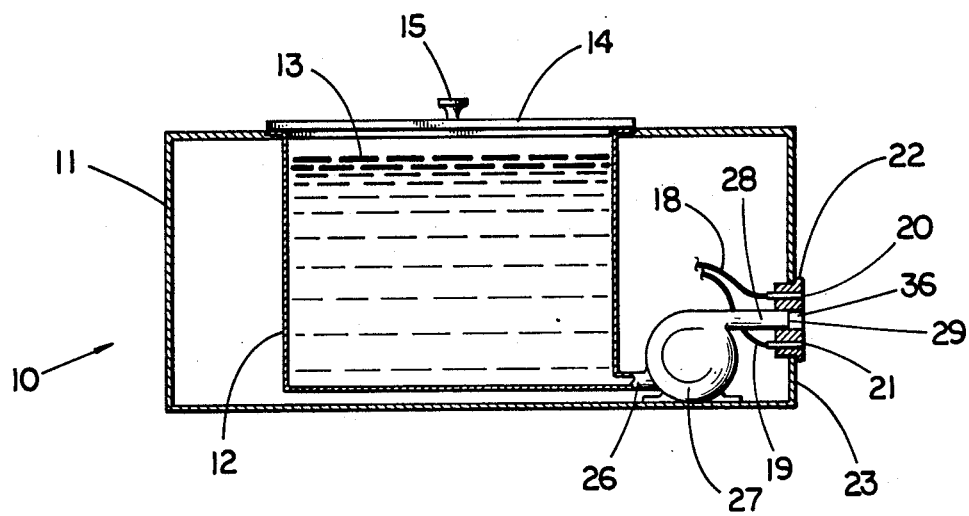
FIG. 2 is a sectioned elevational view of the FIG. 1 control unit taken along line 2—2 in FIG. 1.

Referring to FIGS. 1 and 2, there is illustrated a control unit 10 which comprises a housing 11, a fluid compartment 12 within housing 11, a lid 14 fitted atop and enclosing compartment 12 and a knob 15 attached to lid 14. Wire 16 connects to a source of power (not shown) and inputs to housing 11. ON/OFF switch 17 controls the application of power across wire 6 so as to control whether or not control unit 10 is energized or shut off. The end of wire 16 which connects to housing 11 is joined within control unit 10 to wires 18 and 19 which couple to connectors 20 and 21, respectively. Plug retainer 22 is inserted within wall 23 of housing 11 and is secured in place by means of screws 24 and 25. At the base of compartment 12 which is shown as filled with fluid 13 is a drain aperture 26 which joins to an inlet tube comprising a portion of fluid delivery pump 27. The discharge tube 28 of pump fits within a cylindrical opening 36 within plug retainer 22. As shown, the end 29 of discharge tube 28 is inserted approximately midway into opening 36 in plug retainer 22. The front of control unit 10 also includes a timer 30 which is used to set the duration of the ultrasonic vibrations which the control unit 10 produces when switch 17 is in the "ON" position, as will be described in greater detail later. The operation of timer 30 is such that even with ON/OFF switch 17 in the ON position ultrasonic vibrations will not be generated until timer 30 is set for a certain time interval. The markings around timer 30 are to indicate seconds extending from zero back to zero for a full cycle of one minute. Although other dial durations could be designed, timer 30 is shown to indicate that even the unit "ON," nothing occurs until some time is set. When the timer counts down and returns to zero, the unit will be turned "OFF" and will no longer generate ultrasonic vibrations until additional time is set. Pump 27 is designed for pumping fluid 13 from within compartment 12 through discharge tube 28 to an external location, such as an anatomical cavity. With discharge tube 28 connected to a delivery tube and the cavity filled with fluid, back pressure will be encountered at the location of this cavity and this back pressure will cause pump 27 to shut itself off thereby discontinuing the further delivery of fluid 13 from compartment 12. A final feature of control unit 10 is that a current interrupter (not shown) is coupled to wires 18 and 19 and is capable of stopping current flow in a few milliseconds in the event there is a short circuit or electrical malfunction.

Figure 3:
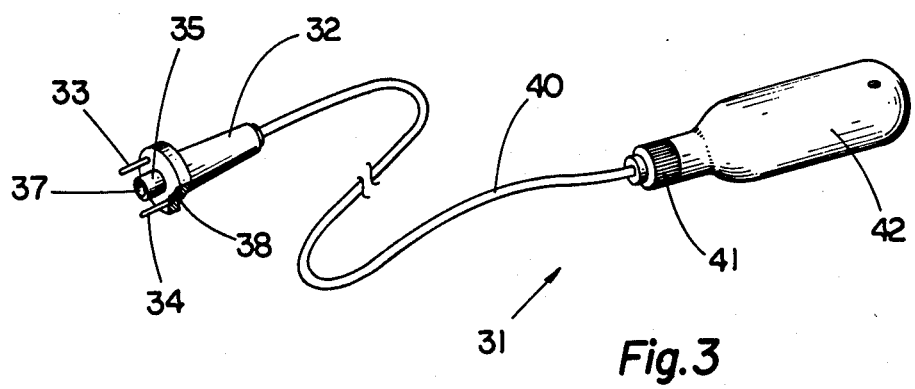
FIG. 3 is a perspective view of an ultrasonic implement and control cable comprising a portion of the device according to the present invention.

Referring to FIG. 3, there is illustrated the remainder of the oral and personal hygiene device according to the present invention. Ultrasonic attachment 31 which is detachable from control unit 10 includes plug member 32 which is insertable into plug retainer 22 for electrical and fluid transfer connections. When plug 32 is inserted into plug retainer 22, pins 33 and 34 will be inserted into and mate with connectors 20 and 21, respectively. Tubular portion 35 fits within cylindrical opening 36 (see FIG. 2) which is left by discharge tube 28 only being inserted approximately half way into plug retainer 22. The end 37 off tubular portion 35 will be pushed against end 29 of discharge tube 28 and inasmuch as there is a snug fit within plug retainer 22 of discharge tube 28 and tubular portion 35, this arrangement will be basically a sealeed connection allowing fluid to be transferred through plug retainer 22 without any noticeable leakage. Within the enlarged flange portion of plug 32, there is shown a wire 38 which connects to pin 34. It will be shown in FIG. 4 that a similar wire connects to pin 33 and that these wire and pin connections transfer power from wires 18 and 19 through connectors 20 and 21, respectively, into a transducer member which is positioned within ultrasonic attachment 31. Plug 32 is connected by means of wire 40 (a cable containing two wires) to a plug 41 which joins to ultrasonic implement 42.

Figure 4:
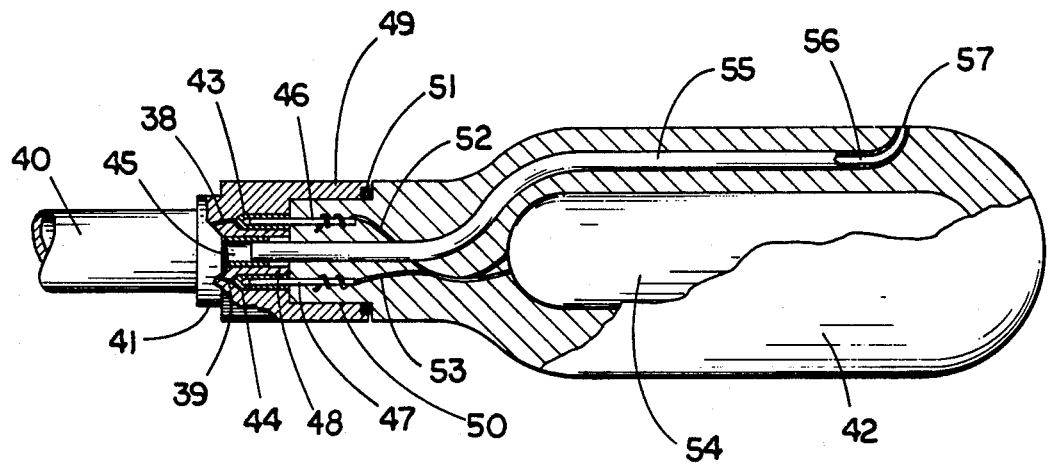
FIG. 4 is an enlarged, fragmentary view of the FIG. 3 ultrasonic implement.

FIG. 4 is a fragmentary detailed view, somewhat enlarged, showing the internal details of ultrasonic implement 42. Wire 40 and plug 41 are only partially shown for purposes of orienting the view of FIG. 4. As shown wires 38 and 39 which connect to pins 34 and 33, respectively, join at their other ends to connectors 43 and 44, respectively. Insertable within connectors 43 and 44 are a pair of contact pins 46 and 47, respectively. Extending through wire 40 from tubular portion 35 is inner tube 45 which is positioned approximately in the center of the end of ultrasonic implement 42. A tubular extension 48 abuts to the end of inner tube 45 thereby attempting to make a sealed connection for the passage of fluid 13 from compartment 12 to ultrasonic implement 42. The cylindrical portion 49 of plug 41 fits around the cylindrical portion 50 of ultrasonic implement 42. Between these two cylindrical portions an O-ring 51 is placed andd serves as a seal between plug 41 and ultrasonic implement 42. Wires 52 and 53 connect to pins 46 and 47, respectively and transfer electrical inputs from control unit 10 to transducer 54. As described, implement 42 is disconnectable from plug 41 such that different implements can be used with a single wire 40, lug 41 and control unit 10. Transducer 54 which may be comprised of nickel-iron laminations or ceramic piezoelectric material responds in the form of ultrasonic vibration to incoming electrical signals which are delivered by control unit 10. Tube 55 is inserted through tubular extension 48 and into inner tube 45 thereby enhancing the sealed connection between tubular extension 48 and inner tube 45 and further providing a path for fluid 13 from compartment 12 through passageway 56 to hole 57 which exits at the surface of ultrasonic implement 42. The device which has been described generates electrical signals which cause a transducer 54 to generate ultrasonic vibrations. In addition, fluid from compartment 12 is delivered at the location of ultrasonic implement 42 and acts with the ultrasonic implement 42 to effect a thorough cleansing action within the particular human anatomical cavity into which ultrasonic implement 42 is inserted. In operation, control unit 10 pumps fluid 13 into the particular anatomical cavity until back pressure turns off pump 27. When timer 30 is set for a particular duration, ultrasonic vibrations are transmitted from implement 42 through the fluid in the cavity to the interior surfaces of the cavity which are cleansed.

Figure 5:
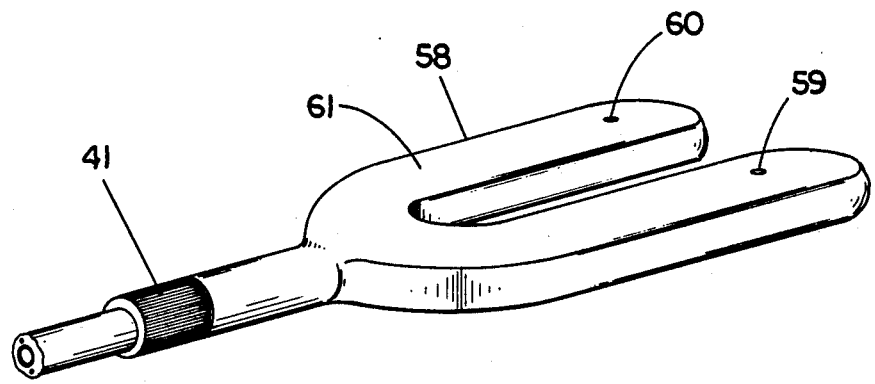
FIG. 5 is a perspective view of an alternate form of an ultrasonic implement comprising a portion of the device according to the present invention.
Figure 6:
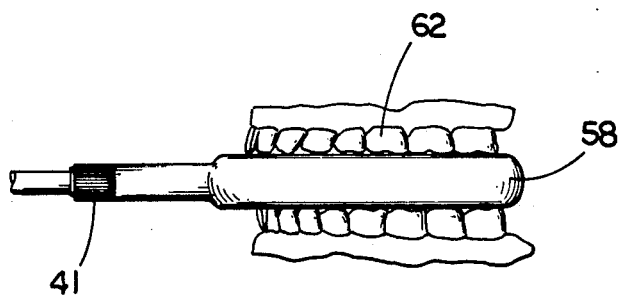
FIG. 6 is a side elevational view of a set of teeth clamping the FIG. 5 ultrasonic implement.

FIG. 5 illustrates an alternate form of an ultrasonic implement 58 which is usable within the control unit 10 in a manner similar to what has been described for ultrasonic implement 42. Ultrasonic implement 58 is connected to wire 40 by means of plug 41 as previously described and discussed. Ultrasonic implement 58 is U-shaped having a pair of flat extending arms, the end of each being adapted with holes 59 and 60 through which fluid 13 from compartment 12 will exit by means of tubes similar to tube 55. Implement 58 is suitably sized and arranged to simultaneously contact the upper surface of the lower row of teeth and the lower surface of the upper row of teeth so as to be operable to cleanse all of the teeth simultaneously. Although the shape of the transducer member which is used within ultrasonic implement 58 is positioned somewhat differently than transducer 54 within ultrasonic implement 42, the transducer member extends only into the base of the U-shaped portion of ultrasonic implement 58. An alternate form of ultrasonic implement 58 is possible by positioning a pair of smaller transducer members in each of the flat extending arms. The surface coating 61 of ultrasonic implement 58 is of a soft, flexible yet durable coating which is substantially nontoxic and physiologically inert. A suitable coating is an organic polymer compound such as silicone. This soft, flexible coating is of a thickness which allows the teeth of a human to be partially embedded as is shown by FIG. 6. The ultrasonic vibrations caused by the transducer within ultrasonic implement 58 are communicated from the transducer through the surface coating 61 to the ends of the teeth 62. Although fluid is introduced into the oral cavity to assist the cleaning efforts of ultrasonic implement 58, the primary advantage of slightly embedding the teeth 62 into surface coating 61 of ultrasonic implement 58 is to provide more direct contact to the ultrasonic vibrations and thereby serves to loosen and remove more stubborn food particles, plaque and other foreign matter. The size and shape of ultrasonic implement 58 is such that it is usable with a variety of individual jaw sizes inasmuch as the arms of the U-shaped portion are somewhat longer than a human jaw. The arms are also wider than the width of an individual row of teeth thereby allowing size flexibility for a range of users.

Figure 7:
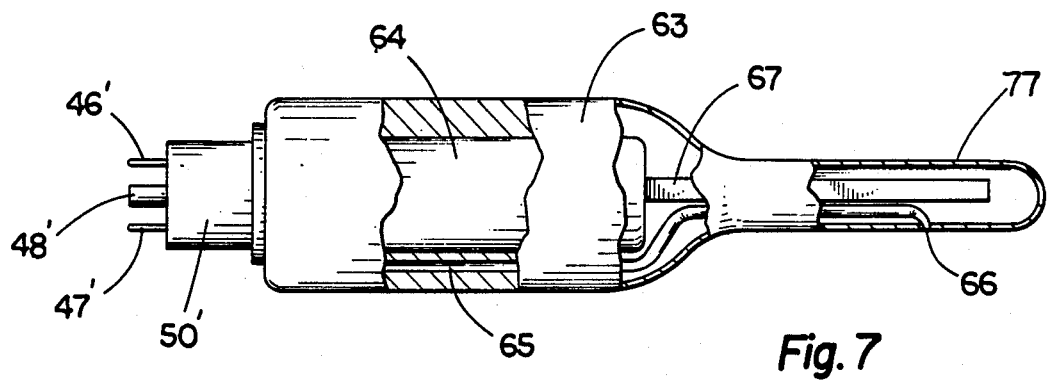
FIG. 7 is a fragmentary side elevational view of an alternate form of an ultrasonic implement according to the present invention.

Referring to FIG. 7, there is illustrated an alternate design for an ultrasonic implement. Prime designations 46', 47', 48' and 50' have been used to orient ultrasonic implement 63 to the remainder of the hygiene device by showing these representative pin and tube connections which mate with wire 40 and plug 41 as previously detailed in FIG. 4. Ultrasonic implement 63 includes an additional feature which has not been previously shown. Although transducer 64, tube 65 and hole 66 are of the same general construction and same theory of operation as previously described, the additional feature of arm 67 is provided so that the ultrasonic implement 63 can be used in situations where there is not the ability or size to insert the entire transducer contained ultrasonic implement into the anatomical cavity. Arm 67 is rigidly attached to transducer 64 and receives the ultrasonic vibrations from transducer 64 thereby transmitting these vibrations to the extended, protruding tip 77 which is the portion which is inserted into the anatomical cavity. This type of design is usable with different ultrasonic implements and although the nature of the ultrasonic vibration in arm 67 may be slightly less than what would be encountered if in direct contact with transducer 64, the device is the only means possible to effect ultrasonic cleansing of openings and cavities which are inaccessible to the larger transducer or in situations where the patient cannot support the size or weight of the entire transducer and ultrasonic implement combination.

Figure 8:
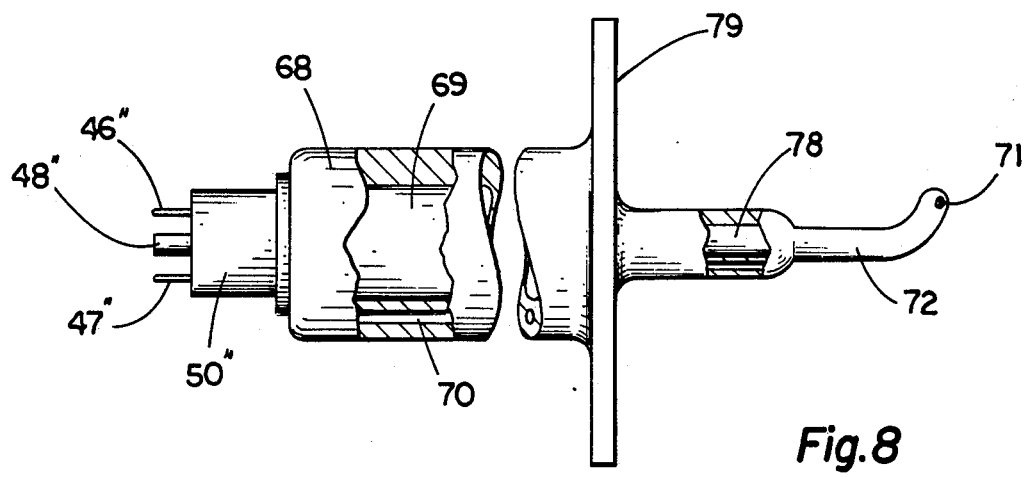
FIG. 8 is a fragmentary side elevational view of an alternate form of a ultrasonic implement according to the present invention.

FIG. 8 is a slightly enlarged fragmentary elevational view of an alternate design of ultrasonic transducer and ultrasonic implement. Again, a double prime reference has been used for pins 46" and 47", for tube 48" and for cylindrical portion 50". Ultrasonic implement 68 includes a transducer 69, tube 70, arm 78, tip 72 and hole 71. Arm 78 which is attached to transducer 69 functions in much the same way as arm 67 functioned with respect to transducer 64 of FIG. 7. The shape of tip 72 is specifically designed for use in cleaning a human's ear. Tip 72 is soft and flexible so that it can be snugly positioned within the ear without causing injury or discomfort to the patient. Hole 71 is used to deliver fluid 13 through tube 70 which is connected to tube 48" and to compartment 12. The introduction of fluid through hole 71 and the ultrasonic vibrations induced in tip 72 by means of arm 78 permit hardened wax deposites within the ear to be softened and vibrated free so that they can be removed without the necessity to poke, gouge or dig into the ear which is often quite painful to the patient. Flange 79 serves as a type of positioning device such that with the ear horizontal, flange 79 will rest against the outer surface allowing tip 72 to be suspended into the external auditory meatus.

Figure 9:
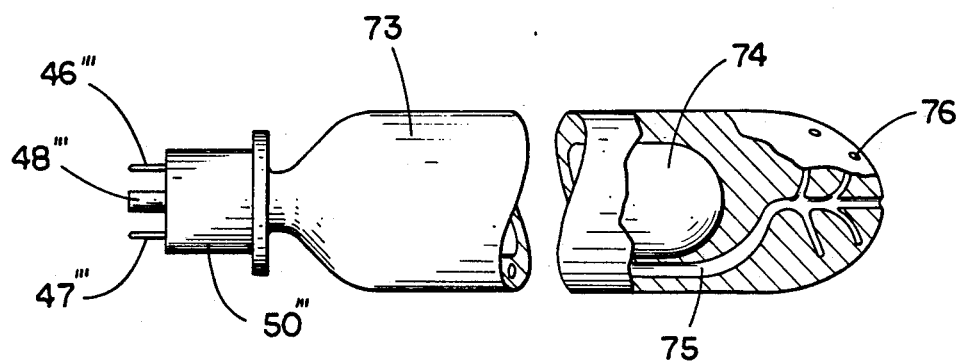
FIG. 9 is a fragmentary side elevational view of an alternate form of an ultrasonic implement according to the present invention.

Referring to FIG. 9, there is shown yet another form of an ultrasonic implement 73 which is also attachable to wire 40 and plug 41 by means of pins 46'" and 47'", tube 48'" and cylindrical portion 50'". Ultrasonic implement 73 includes ultrasonic transducer 74, tube 75 which branches outwardly into a plurality of holes 76. The operation of ultrasonic implement 73 is virtually the same as has been described for implements 42, 58, 63 and 68. The size, shape and design of ultrasonic implement 73 is intended to be used as a vaginal cleansing device for the control of infections and is not intended for daily hygiene use.

As has been previously mentioned, the fluid 13 which is placed within compartment 12 may be of virtually any chemical content. It is intended that the selection of a particular fluid be based upon the intended use for the ultrasonic implement and the nature of the cleansing which is to be performed or the nature of the invention to be curtailed. The ultrasonic implement designs of FIGS. 4, 5 and 6 which are intended primarily for dental uses, would normally have a flavored cleansing or antibacterial detergent mixed with water to comprise fluid 13. This mixture would serve much the same purpose as toothpaste presently does. Minor abrasives could also be added in the event a stronger acting cleansing fluid was desired. The ultrasonic implement of FIG. 8 which was disclosed as being primarily intended for cleaning the ear would have a fluid comprised of a detergent and emulsifier specifically designed to break up and dissolve wax deposits. The ultrasonic implement of FIG. 9 which is intended for vaginal cleansing would normally be used with a fluid comprised of saline and either antibiotic or antiyeast medication inasmuch as the intended use is to control infections.

It is contemplated within the scope of this invention that other shapes, sizes and configurations of ultrasonic implements could be configured based on such variables as the size and shape of the human cavity which is to be cleansed. Such alternate forms are to be anticipated within the scope of the present application.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An oral and personal hygiene device for cleansing various anatomical cavities which comprises:
   a fluid compartment having a drain aperture therein;
   means for generating ultrasonic vibrations including an ultrasonic transducer;
   an ultrasonic implement constructed of a size and shape so as to be insertable within one of said anatomical cavities, said ultrasonic implement enclosing said transducer and having a passageway therethrough for the passage of fluid to fill said cavity;
   a fluid delivery device connected between said drain aperture and said ultrasonic implement for the delivery of fluid from said compartment to the cavity into which said ultrasonic implement is inserted;
   said ultrasonic implement communicating ultrasonic vibrations from said transducer to the fluid filling said cavity whereby ultrasonic vibrations are transmitted in the form of cavitating action through the fluid to all internal surfaces of said cavity while said ultrasonic implement remains virtually stationary; and
   a timer electrically coupled to said generated means for controlling the duration of ultrasonic vibrations.

2. The oral and personal hygiene device of claim 1 which further comprises a control unit which includes said compartment and said fluid delivery device and said ultrasonic implement is connectible to said control unit by means of a fluid-carrying tube and electrical wire arrangement.

3. The oral and personal hygiene device of claim 2 in which said ultrasonic implement is disconnectible from said fluid-carrying tube and electrical wire arrangement.

4. The oral and personal hygiene device of claim 3 in which said control unit further includes a current interrupter which is operable to stop current flow in the event of an electrical malfunction.

5. The oral and personal hygiene device of claim 2 in which said fluid delivery device is operable to turn itself off in response to back pressure created when said cavity is filled with fluid.

6. The oral and personal hygiene device of claim 3 in which said ultrasonic implement is sized and shaped to fit within a human's mouth.

7. The oral and personal hygiene device of claim 3 in which said ultrasonic implement is sized and shaped to fit within a human's ear.

8. The oral and personal hygiene device of claim 3 in which said ultrasonic implement is sized and shaped to fit within a female's vagina.

9. The oral and personal hygiene device of claim 6 in which said ultrasonic implement is U-shaped so as to conform to the general curvature of a human's row of teeth.

10. The oral and personal hygiene device of claim 9 in which said ultrasonic implement is covered with a deformable organic polymer compound.

11. An oral and personal hygiene device for cleansing various anatomical cavities which comprises:
    a fluid compartment having a drain aperture therein;
    means for generating ultrasonic vibrations including an ultrasonic transducer;
    an ultrasonic implement constructed of a size and shape so as to be insertable within one of said anatomical cavities, said ultrasonic implement enclosing said transducer and having a passageway therethrough for the passage of fluid to fill said cavity;
    a fluid delivery device connected between said drain aperture and said ultrasonic implement for the delivery of fluid from said compartment to the cavity into which said ultrasonic implement is inserted;
    said ultrasonic implement communicating ultrasonic vibrations from said transducer to the fluid filling said cavity whereby ultrasonic vibrations are transmitted in the form of cavitating action through the fluid to all internal surfaces of said cavity while said ultrasonic implement remains virtually stationary; and
    said fluid delivery device has means operable to turn itself off in response to back pressure created when said cavity is filled with fluid.

12. The oral and personal hygiene device of claim 11 which further comprises a control unit which includes said compartment and said fluid delivery device and said ultrasonic implement is connectable to said unit by means of a fluid-carrying tube and electrical wire arrangement.

13. The oral and personal hygiene device of claim 12 in which said ultrasonic implement is disconnectable from said fluid-carrying tube and electrical wire arrangement.

14. The oral and personal hygiene device of claim 13 in which said control unit further includes a current interrupter which is operable to stop current flow in the event of an electrical malfunction.

15. An oral and personal hygiene device for cleansing a human's teeth which comprises:
    a fluid compartment having a drain aperture therein;
    means for generating ultrasonic vibrations including an ultrasonic transducer;
    an ultrasonic implement having a substantially flat, U-shaped configuration designed and arranged to be contacted simultaneously by each of the teeth in both upper and lower rows of teeth;
    a fluid deliveryy device connected between said drain aperture and said ultrasonic implement for the delivery of fluid from said compartment to the mouth cavity wherein said ultrasonic implement is located; and
    said ultrasonic implement communicating ultrasonic vibration from said transducer to the fluid filling said mouth cavity whereby ultrasonic vibrations are transmitted in the form of cavitating action through the fluid to all external surfaces of said teeth while said ultrasonic implement remains virtually stationary.

16. The oral and personal hygiene device of claim 15 which further comprises a control unit which includes said compartment and said fluid delivery device and said ultrasonic implement is connectible to said control unit by means of a fluid-carrying tube and electrical wire arrangement.

17. The oral and personal hygiene device of claim 16 in which said ultrasonic implement is disconnectible from said fluid-carrying tube and electrical wire arrangement.

18. The oral and personal hygiene device of claim 17 in which said control unit further includes a current interrupter which is operable to stop current flow in the event of an electrical malfunction.

19. The oral and personal hygiene device of claim 18 in which said fluid delivery device is operable to turn itself off in response to back pressure created when said mouth cavity is filled with fluid.

* * * * *